| United States Patent [19] | [11] | 4,088,785 |
|---|---|---|
| Diamond et al. | [45] | May 9, 1978 |

[54] AMIDINOUREAS FOR THE TREATMENT OF CARDIOVASCULAR DISORDERS

[75] Inventors: Julius Diamond, Lafayette Hill; George H. Douglas, Paoli, both of Pa.

[73] Assignee: William H. Rorer, Inc., Fort Washington, Pa.

[21] Appl. No.: 766,656

[22] Filed: Feb. 8, 1977

Related U.S. Application Data

[60] Division of Ser. No. 670,220, Mar. 25, 1976, abandoned, which is a continuation of Ser. No. 486,783, Jul. 9, 1974, abandoned, which is a continuation of Ser. No. 291,474, Sep. 22, 1972, abandoned.

[51] Int. Cl.² .................. A61K 31/17; A61K 31/275; A61K 31/165

[52] U.S. Cl. .................................. 424/322; 424/304; 424/324

[58] Field of Search .................. 424/324, 304, 322

[56] References Cited

U.S. PATENT DOCUMENTS

| 4,013,643 | 3/1977 | Nysted | 424/324 |
|---|---|---|---|
| 4,015,011 | 3/1977 | Schromm et al. | 424/324 |
| 4,045,483 | 8/1977 | Cutler et al. | 424/322 |

Primary Examiner—Sam Rosen
Attorney, Agent, or Firm—James A. Nicholson; John C. Smith, Jr.

[57] ABSTRACT

Novel substituted phenylamidinourea compounds and processes for their preparation are disclosed. A method for the treatment of hypertensive disorders is also described.

6 Claims, No Drawings

AMIDINOUREAS FOR THE TREATMENT OF CARDIOVASCULAR DISORDERS

CROSS REFERENCE TO RELATED APPLICATIONS

This application is a Division of Ser. No. 670,222 filed Mar. 25, 1976; which is a continuation of Ser. No. 486,783 filed July 9, 1974; which is a continuation of Ser. No. 291,474 filed Sept. 22, 1977, all now abandoned.

SUMMARY OF THE INVENTION

This invention describes new substituted phenylamidinourea compounds and processes for their preparation. This invention further provides valuable pharmaceutical preparations which contain substituted phenylamidinourea compounds which possess an effective degree of antihypertensive properties and exert activities on the cardiovascular system. A method for the treatment of hypertensive disorders by the administration of a substituted phenylamidinourea compound is also described.

BACKGROUND OF THE INVENTION

The pharmaceutical compositions which have been used as antihypertensive agents have included such as the thiazides, reserpine, hydralazine, α-methyl dopa, quanethidine and the like. These compounds, however, while being effective produce undesirable side effects such as electrolyte inbalance, orthostatic hypertension, and gastric secretory and spasmolytic properties.

I have unexpectedly found that amidinourea compounds exhibit valuable pharmacologic properties.

I have unexpectedly found that the amidinoureas of this invention are useful antihypertensive agents.

I have further found that the amidinoureas compounds of this invention are novel and can easily be prepared.

I have also found that the compounds of this invention have a minimum of the side effects which accompany antihypertensive agents.

I have still further found a simple and effective method for the treatment of cardiovascular disorders such as hypertensive disorders.

DESCRIPTION AND PREFERRED EMBODIMENT

This invention describes a class of novel chemical compounds which comprises a substituted phenyl radical which is further attached to an amidinourea chain. This results in urea type compounds having a substituted phenylamidino group attached at one of the nitrogen atoms. This invention also describes the non-toxic pharmaceutically acceptable salts and the method of preparing these substituted phenylamidinourea compounds.

The novel compounds of this invention are described by the structural formula I

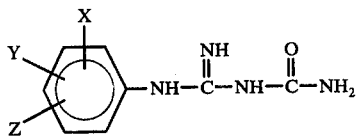

where:

X is hydrogen or halo;
Y is hydrogen, halo, haloloweralkyl, nitro, loweralkyl or loweralkoxy;
Z is haloloweralkyl, haloloweralkoxy or loweralkysulfonyl;
Z is also halo, loweralkoxy, loweralkyl, nitro or cyano provided X and Y are not both hydrogen at the same time;

and the non-toxic acid addition salts thereof.

Compounds of this invention which are preferred are described by general formula I
where:
X is hydrogen or halo;
Y is hydrogen, halo, loweralkyl or haloloweralkyl; and
Z is halo or loweralkyl (provided X and Y are not both hydrogen) or haloloweralkyl.

The more preferred compounds of this invention include those compounds
where:
X is hydrogen, chloro, bromo or fluoro;
Y is hydrogen, chloro, bromo, fluoro, methyl or trifluoromethyl and
Z is chloro provided X and Y are not both hydrogen, bromo provided X and Y are not both hydrogen, fluoro provided X and Y are not both hydrogen, methyl provided X and Y are not both hydrogen or trifluoromethyl.

This invention further describes a new method for the treatment of cardiovascular disorders by the administration of a therapeutically effective amount of an amidinourea compound of formula II

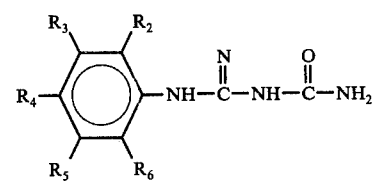

where:
$R_2$, $R_3$, $R_4$, $R_5$ and $R_6$ may be the same or different and are hydrogen (provided at least one of $R_2$, $R_3$, $R_4$, $R_5$ and $R_6$ is other than hydrogen), halo, haloloweralkyl, nitro, cyano, loweralkylsulfonyl, loweralkoxy or loweralkyl; and
the non-toxic acid addition salts thereof.

The preferred compounds which are useful in the treatment of cardiovascular disorders are exemplified by those compounds of formula III

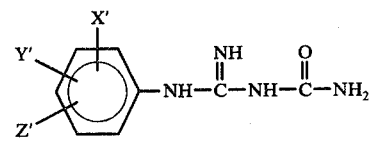

where:
X', Y' and Z' may be the same or different and are hydrogen (provided at least one of X', Y' and Z' is other than hydrogen), halo, haloloweralkyl, nitro, cyano, loweralkylsulfonyl, loweralkoxy or loweralkyl.

The more preferred compounds which are useful in the treatment of cardiovascular disorders are shown in formula III where:
X', Y' and Z' are hydrogen (provided at least one of X', Y' and Z' is other than hydrogen), halo, haloloweralkyl or loweralkyl.

The most preferred compounds are described by formula III
where:
X' is hydrogen, chloro bromo or fluoro;
Y' is hydrogen, chloro, methyl or trifluoromethyl;
Z' is chloro, bromo, fluoro, methyl or trifluoromethyl.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc., and include such as:

| | |
|---|---|
| hydrochloric acid, | succinic acid, |
| hydrobromic acid, | glycolic acid, |
| sulfuric acid, | lactic acid, |
| nitric acid, | salicylic acid, |
| phosphoric acid, | benzoic acid, |
| methane sulfonic acid, | nicotinic acid, |
| benzene sulfonic acid, | phthalic acid, |
| acetic acid, | stearic acid, |
| propionic acid, | oleic acid, |
| malic acid, | abietic acid, etc. |

Representative compounds of this invention which are particularly useful are as follows:

o-chlorophenylamidinourea
m-chlorophenylamidinourea
p-chlorophenylamidinourea
(2,3-dichlorophenylamidino)urea
(2,4-dichlorophenylamidino)urea
(2,5-dichlorophenylamidino)urea
(2,6-dichlorophenylamidino)urea
(3,4-dichlorophenylamidino)urea
(3,5-dichlorophenylamidino)urea
(2,3,4-trichlorophenylamidino)urea
(2,3,5-trichlorophenylamidino)urea
(2,3,6-trichlorophenylamidino)urea
(2,4,5-trichlorophenylamidino)urea
(2,4,6-trichlorophenylamidino)urea
(3,4,5-trichlorophenylamidino)urea
o-bromophenylamidinourea
m-bromophenylamidinourea
p-bromophenylamidinourea
(2,3-dibromophenylamidino)urea
(2,4-dibromophenylamidino)urea
(2,5-dibromophenylamidino)urea
(2,6-dibromophenylamidino)urea
(3,4-dibromophenylamidino)urea
(3,5-dibromophenylamidino)urea
(2-chloro-3-bromophenylamidino)urea
(2-chloro-4-bromophenylamidino)urea
(2-chloro-5-bromophenylamidino)urea
(2-chloro-6-bromophenylamidino)urea
(3-chloro-2-bromophenylamidino)urea
(3-chloro-4-bromophenylamidino)urea
(3-chloro-5-bromophenylamidino)urea
(3-chloro-6-bromophenylamidino)urea
(4-chloro-2-bromophenylamidino)urea
(4-chloro-3-bromophenylamidino)urea
(2-fluoro-4-chlorophenylamidino)urea
(2-fluoro-6-chlorophenylamidino)urea
(2-chloro-4-fluorophenylamidino)urea
(2-fluoro-6-bromophenylamidino)urea
(2-bromo-4-fluorophenylamidino)urea
(2-iodo-4-chlorophenylamidino)urea
(2-iodo-6-chlorophenylamidino)urea
(2-chloro-4-iodophenylamidino)urea
(2-iodo-4-bromophenylamidino)urea
o-fluorophenylamidinourea
m-fluorophenylamidinourea
p-fluorophenylamidinourea
p-iodophenylamidinourea
(2,4-difluorophenylamidino)urea
(2,5-difluorophenylamidino)urea
(2,6-difluorophenylamidino)urea
(2,4-diiodophenylamidino)urea
(2-iodo-6-bromophenylamidino)urea
(2-bromo-4-iodophenylamidino)urea
(2-fluoro-4-iodophenylamidino)urea
(2-iodo-4-fluorophenylamidino)urea
(2,4-dichloro-6-bromophenylamidino)urea
(2,6-dichloro-4-bromophenylamidino)urea
(2,4-dibromo-6-chlorophenylamidino)urea
(2,6-dibromo-4-chlorophenylamidino)urea
(2,4-dichloro-6-fluorophenylamidino)urea
(2,6-dichloro-4-fluorophenylamidino)urea
(2,5-dichloro-4-fluorophenylamidino)urea
(2,4-dichloro-6-iodophenylamidino)urea
(2,6-dichloro-4-iodophenylamidino)urea
(2,4-dibromo-6-iodophenylamidino)urea
(2,4-dibromo-6-fluorophenylamidino)urea
(2,6-dibromo-4-fluorophenylamidino)urea
(2-chloro-4-bromo-6-fluorophenylamidino)urea
(2-bromo-4-fluoro-6-chlorophenylamidino)urea
(2-bromo-4-chloro-6-fluorophenylamidino)urea
(2-chloro-4-iodo-6-bromophenylamidino)urea
(2,4,6-trifluorophenylamidino)urea
o-trifluoromethylphenylamidinourea
m-trifluoromethylphenylamidinourea
p-trifluoromethylphenylamidinourea
p-trifluoromethoxyphenylamidinourea
p-methylsulfonylphenylamidinourea
(2-chloro-4-nitrophenylamidino)urea
(2-bromo-4-nitrophenylamidino)urea
(2-iodo-4-nitrophenylamidino)urea
(2-fluoro-4-nitrophenylamidino)urea
(2-nitro-4-chlorophenylamidino)urea
(2-nitro-4-bromophenylamidino)urea
(2-nitro-4-fluorophenylamidino)urea
(2-nitro-4-trifluoromethylphenylamidino)urea
(2-nitro-4-methoxyphenylamidino)urea
(2-cyano-4-chlorophenylamidino)urea
(2-chloro-4-cyanophenylamidino)urea
(2-methyl-4-chlorophenylamidino)urea
(2-methyl-4-bromophenylamidino)urea
(2-methyl-4-fluorophenylamidino)urea
(2-methyl-4-nitrophenylamidino)urea
(2-methyl-4-cyanophenylamidino)urea
(2-methyl-4-trifluoromethylphenylamidino)urea
(2,4-dimethylphenylamidino)urea
(2,6-dimethylphenylamidino)urea
(2,6-dimethyl-4-chlorophenylamidino)urea
(2,6-dimethyl-4-fluorophenylamidino)urea (2,6-dimethyl-4-bromophenylamidino)urea
(2,6-dimethyl-4-nitrophenylamidino)urea
(2,6-dimethyl-4-trifluoromethylphenylamidino)urea
(2-chloro-4-methylphenylamidino)urea
(2-bromo-4-methylphenylamidino)urea
(2-fluoro-4-methylphenylamidino)urea
(2-nitro-4-methylphenylamidino)urea
(2,6-dichloro-4-methylphenylamidino)urea
(2,4-dichloro-6-nitrophenylamidino)urea
(2,6-dichloro-4-nitrophenylamidino)urea
(2-ethyl-4-nitrophenylamidino)urea
(2-ethyl-4-chlorophenylamidino)urea
(2-ethyl-4-bromophenylamidino)urea
(2-ethyl-4-fluorophenylamidino)urea
(2-ethyl-4-trifluorophenylamidino)urea
(2-cyano-4-methylphenylamidino)urea
(2-trifluoromethyl-4-methylphenylamidino)urea
(2-trifluoromethyl-6-chlorophenylamidino)urea
(4-trifluoromethyl-2-chlorophenylamidino)urea
(4-trifluoromethyl-2-bromophenylamidino)urea
(4-trifluoromethyl-2-fluorophenylamidino)urea
(2,4-dichloro-6-methylphenylamidino)urea
(2,6-dichloro-6-methylphenylamidino)urea
(3,5-ditrifluoromethylphenylamidino)urea
(2-trifluoromethyl-4-nitrophenylamidino)urea
(2-methoxy-4-nitrophenylamidino)urea
(2,4-dichloro-6-methoxyphenylamidino)urea The compounds of this invention may be prepared by the following general synthesis:

Condensation of cyanamide and a substituted aniline results in the corresponding substituted phenylguanidine.

The reaction is preferably carried out on the aniline salt either in a polar medium or neat and using increased temperatures. The salt used may be any acid addition amine salt but preferably the salt of a mineral acid. The polar medium may be aqueous, partially aqueous or a non-aqueous solution. It is convenient to choose a solvent that will reflux at the desired reaction temperature. The more preferred solvents are water or alcohol but other solvents may be used such as DMSO, diethyleneglycol, ethyleneglycol, tetrahydrofuran, dimethylformamide, etc. The most preferred solvent is a mildly acidic solvent which is non-nucleophilic such as phenol, cresol, xyenol, etc. The reaction should also be carried out at a temperature which is high enough so that condensation takes place readily, but not sufficient to decompose the guanidine formed. The reaction temperature can very from room temperature to about 250° C although it is preferable to run the reaction at temperatures from about 50° C to 150° C. The guanidine salt which is formed can be converted to the free base with a metal hydroxide or alkoxide solution. The isolation of the desired guanidine can be carried out by any method known in the art.

When the substituted phenylguanidine is reacted with t-butylisocyanate then the product formed is a 1-substituted phenylamidino-3-t-butylurea. This reaction is preferably carried out in a non-polar medium using solvents such as benzene, toluene, xylene, etc. The reaction is also carried out as above at raised temperatures.

Treatment of the 1-substituted phenylamidino-3-t-butylurea with acid results in the desired 1-substituted phenylamidinourea. This reaction is carried out preferably as a 10% solution in a 1:1 mixture of conc. hydrochloric acid and glacial acetic acid at increased temperature. The resultant product is isolated as a salt by any method known in the art.

The following reaction equations illustrate this synthesis:

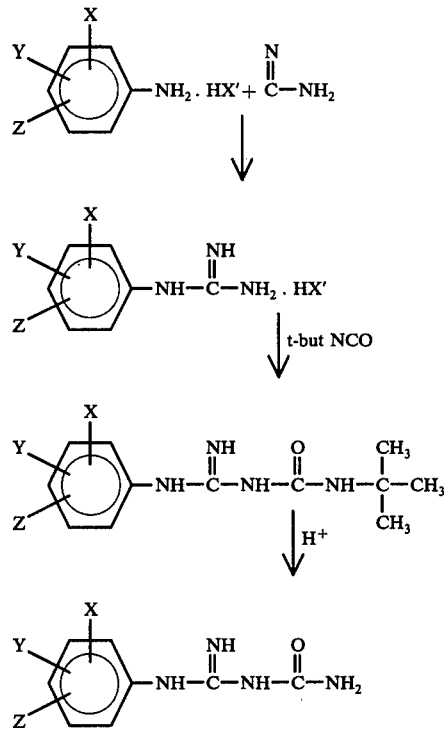

where:

HX' is a mineral acid.

Appropriately desired end products having various X, Y and Z substituents may be prepared at various steps of synthesis using suitable reactions in order to convert one group to another.

The starting anilines are either known, may be prepared by known techniques or reference to the preparation is shown. Thus, chlorination or bromination of an acetanilide or aniline may be carried out in acetic acid, or in the presence of a small amount of iodine dissolved in an inert solvent such as carbon tetrachloride. A solution of chlorine or bromine is then added while the temperature is held near 0° C. Iodination may also be carried out by known methods using iodine monochloride (CII).

Alkylation may be carried out on an acetanilide using an alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonium fluoroborate which is then thermally decomposed to the fluoro compound. Diazotization followed by a Sandmeyer type reaction may yield the bromo, chloro or iodo compound.

Diazotization of an amino compound followed by addition of cuprous cyanide may result in the desired cyano compound.

When an amino compound is diazotized followed by reaction with potassium ethylxanthate and then hydrolyzed, the mercapto compound results. This in turn may be alkylated to the alkylthio group which is then oxidized to the corresponding alkylsulfonyl substituent.

A halo compound in which halo is chloro or bromo or iodo may be reacted with cuprous cyanide in guanidine at about 150° C to produce a cyano compound.

A chloro, bromo or iodo compound may also be reacted with trifluoromethyliodide and copper powder at about 150° C in dimethylformamide to obtain a trifluoromethyl compound [Tetrahedron Letters: 47, 4095 (1959)]

A halo compound may also be reacted with cuprous methanesulfinate in quinoline at about 150° C to obtain a methylsulfonyl compound.

Of course any of the above reactions may also be carried out on acetophenone in order to direct substitution. Formation of an oxime followed by Beckmann Rearrangement results in the acetamide which is then deacylated to the aniline.

Reactions may also be carried out on the substituted anilines which would result in di- and tri- substituted anilines.

Reactions may also be carried out at other stages of synthesis depending on the substituents present and the substituents desired and various combinations of the foregoing reactions will be determined by one skilled in the art in order that the desired product results. Thus, a phenylguanidine may be halogenated or nitrated as above, etc.

The compounds of this invention exert activity on the cardiovascular system. They possess blood-pressure lowering effects and are useful as antihypertensive agents.

For these purposes, the amidinoureas of this invention can be normally administered orally or parenterally. Orally they may be administered as tablets, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents, preserving agents and the like, in order to provide a pharmaceutically elegant and palatable preparation.

The dosage regimen in carrying out the methods of this invention is that which insures maximum therapeutic response until improvement is obtained and thereafter the minimum effective level which gives relief. Thus, in general, the dosages are those that are therapeutically effective in the alleviation of hypertensive disorders. In general, the daily dose can be between about 0.05 mg/kg/day and 70 mg/kg/day (preferably in the range of 1-25 mg/kg/day), bearing in mind, of course, that in selecting the appropriate dosage in any specific case, consideration must be given to the patient's weight, general health, age, and other factors which may influence response to the drug.

Various tests in animals have been carried out to show the ability of the compounds of this invention to exhibit reactions that can be correlated with activity in humans.

One such test is the ability of the compound to lower blood pressure in the spontaneous hypertensive rat (Ryo Tabei, et al., Clin. Pharm. & Therap. 11: 269–274, 1970). Blood pressure measurements are recorded by both the tail cuff method and by direct cannulation of a common carotid artery. Compounds that are effective antihypertensives in man have been shown to be active in lowering blood pressure in this animal model. In view of the results of this test, the amidinoureas of this invention can be considered to be active antihypertensive agents.

The following are detailed examples which show the preparation of the compounds of this invention. They are to be construed as illustrations of said compounds and not as limitations thereof.

EXAMPLE 1

2,6-Dichlorophenylguanidine

To 51 g. (0.315 mole) of 2,6-dichloroaniline is added 0.4 moles of etherial HCl and 200 ml of m-cresol. The mixture is then stirred and heated on a steam bath to drive off the ether and excess hydrogen chloride. To the resultant mixture is then added 13.3 g. (0.315 mole) of cyanamide then heated for 2 hours on a steam bath. The reaction mixture is then cooled, added to 150 ml of conc. sodium hydroxide solution, cooled and extracted with 2 liters of ether. The ether layer is washed with 2 × 1 liter of water, dried over sodium sulfate, charcoaled and evaporated. The residue is triturated with hexane and the precipitate is filtered off and washed with ether and dried to obtain 2,6-dichlorophenylguanidine.

The free base is prepared by dissolving 2,6-dichlorophenylguanidine hydrochloride in 10% sodium hydroxide solution and extracting with ether. The ether is dried and evaporated to dryness to obtain 2,6-dichlorophenylguanidine.

When the above procedures are followed using the amines of Table I, below, then the corresponding product of Table II, below, is prepared.

| TABLE I | TABLE II |
|---|---|
| o-chloroaniline | o-chlorophenylguanidine |
| m-chloroaniline | m-chlorophenylguanidine |
| p-chloroaniline | p-chlorophenylguanidine |
| 2,3-dichloroaniline | 2,3-dichlorophenylguanidine |
| 2,4-dichloroaniline | 2,4-dichlorophenylguanidine |
| 2,5-dichloroaniline | 2,5-dichlorophenylguanidine |
| 3,4-dichloroaniline | 3,4-dichlorophenylguanidine |
| 3,5-dichloroaniline | 3,5-dichlorophenylguanidine |
| 2,3,4-trichloroaniline | 2,3,4-trichlorophenylguanidine |
| 2,3,5-trichloroaniline | 2,3,5-trichlorophenylguanidine |
| 2,3,7-trichloroaniline | 2,3,6-trichlorophenylguanidine |
| 2,4,5-trichloroaniline | 2,4,5-trichlorophenylguanidine |
| 2,4,6-trichloroaniline | 2,4,6-trichlorophenylguanidine |
| 3,4,5-trichloroaniline | 3,4,5-trichlorophenylguanidine |
| o-bromoaniline | o-bromophenylguanidine |
| m-bromoaniline | m-bromophenylguanidine |
| p-bromoaniline | p-bromophenylguanidine |

-continued

| TABLE I | TABLE II |
|---|---|
| 2,3-dibromoaniline | 2,3-dibromophenylguanidine |
| 2,4-dibromoaniline | 2,4-dibromophenylguanidine |
| 2,5-dibromoaniline | 2,5-dibromophenylguanidine |
| 2,6-dibromoaniline | 2,6-dibromophenylguanidine |
| 3,4-dibromoaniline | 3,4-dibromophenylguanidine |
| 3,5-dibromoaniline | 3,5-dibromophenylguanidine |
| 2-chloro-3-bromoaniline | 2-chloro-3-bromophenylguanidine |
| 2-chloro-4-bromoaniline | 2-chloro-4-bromophenylguanidine |
| 2-chloro-5-bromoaniline | 2-chloro-5-bromophenylguanidine |
| 2-chloro-6-bromoaniline | 2-chloro-6-bromophenylguanidine |
| 3-chloro-2-bromoaniline | 3-chloro-2-bromophenylguanidine |
| 3-chloro-4-bromoaniline | 3-chloro-4-bromophenylguanidine |
| 3-chloro-5-bromoaniline | 3-chloro-5-bromophenylguanidine |
| 3-chloro-6-bromoaniline | 3-chloro-6-bromophenylguanidine |
| 4-chloro-2-bromoaniline | 4-chloro-2-bromophenylguanidine |
| 4-chloro-3-bromoaniline | 4-chloro-3-bromophenylguanidine |
| 2-fluoro-4-chloroaniline | 2-fluoro-4-chlorophenylguanidine |
| 2-fluoro-6-chloroaniline | 2-fluoro-6-chlorophenylguanidine |
| 2-chloro-4-fluoroaniline | 2-chloro-4-fluorophenylguanidine |
| 2-fluoro-6-bromoaniline | 2-fluoro-6-bromophenylguanidine |
| 2-bromo-4-fluoroaniline | 2-bromo-4-fluorophenylguanidine |
| 2-iodo-4-chloroaniline | 2-iodo-4-chlorophenylguanidine |
| 2-iodo-6-chloroaniline | 2-iodo-6-chlorophenylguanidine |
| 2-chloro-4-iodoaniline | 2-chloro-4-iodophenylguanidine |
| 2-iodo-4-bromoaniline | 2-iodo-4-bromophenylguanidine |
| o-fluoroaniline | o-fluorophenylguanidine |
| m-fluoroaniline | m-fluorophenylguanidine |
| p-fluoroaniline | p-fluorophenylguanidine |
| p-iodoaniline | p-iodophenylguanidine |
| 2,4-difluoroaniline | 2,4-difluorophenylguanidine |
| 2,5-difluoroaniline | 2,5-difluorophenylguanidine |
| 2,6-difluoroaniline | 2,6-difluorophenylguanidine |
| 2,4-diiodoaniline | 2,4-diiodophenylguanidine |
| 2-iodo-6-bromoaniline | 2-iodo-6-bromophenylguanidine |
| 2-bromo-4-iodoaniline | 2-bromo-4-iodophenylguanidine |
| 2-fluoro-4-iodoaniline | 2-fluoro-4-iodophenylguanidine |
| 2-iodo-4-fluoroaniline | 2-iodo-4-fluorophenylguanidine |
| o-trifluoromethylaniline | 2-trifluoromethylphenylguanidine |
| m-trifluoromethylaniline | m-trifluoromethylphenylguanidine |
| p-trifluoromethylaniline | p-trifluoromethylphenylguanidine |
| p-trifluoromethoxyaniline | p-trifluoromethoxyphenylguanidine |
| p-methylsulfonylaniline | p-methylsulfonylphenylguanidine |
| o-nitroaniline | o-nitrophenylguanidine |
| m-nitroaniline | m-nitrophenylguanidine |
| p-nitroaniline | p-nitrophenylguanidine |
| 2-chloro-4-nitroaniline | 2-chloro-4-nitrophenylguanidine |
| 2-bromo-4-nitroaniline | 2-bromo-4-nitrophenylguanidine |
| 2-iodo-4-nitroaniline | 2-iodo-4-nitrophenylguanidine |
| 2-fluoro-4-nitroaniline | 2-fluoro-4-nitrophenylguanidine |
| 2-nitro-4-chloroaniline | 2-nitro-4-chlorophenylguanidine |
| 2-nitro-4-bromoaniline | 2-nitro-4-bromophenylguanidine |
| 2-nitro-4-fluoroaniline | 2-nitro-4-fluorophenylguanidine |
| 2-nitro-4-trifluoromethylaniline | 2-nitro-4-trifluoromethylphenylguanidine |
| 2-nitro-4-methoxyaniline | 2-nitro-4-methoxyphenylguanidine |
| 2-cyano-4-chloroaniline | 2-cyano-4-cyanophenylguanidine |
| 2-methyl-4-cyanoaniline | 2-chloro-4-cyanophenylguanidine |
| 2-methyl-4-chloroaniline | 2-methyl-4-chlorophenylguanidine |
| 2-methyl-4-bromoaniline | 2-methyl-4-bromophenylguanidine |
| 2-methyl-4-fluoroaniline | 2-methyl-4-fluorophenylguanidine |
| 2-chloro-4-methylaniline | 2-chloro-4-methylphenylguanidine |
| 2-bromo-4-methylaniline | 2-bromo-4-methylphenylguanidine |
| 2-fluoro-4-methylaniline | 2-fluoro-4-methylphenylguanidine |
| 2-cyano-4-methylaniline | 2-cyano-4-methylphenylguanidine |
| 2-trifluoromethyl-4-methylaniline | 2-trifluoromethyl-4-methylphenylguanidine |
| 2-methyl-4-nitroaniline | 2-methyl-4-nitrphenylguanidine |
| 2-methyl-4-cyanoaniline | 2-methyl-4-cyanophenylguanidine |
| 2-methyl-4-trifluoromethylaniline | 2-methyl-4-trifluoromethylphenylguanidine |
| 2-chloro-6-nitroaniline | 2-chloro-6-nitrophenylguanidine |
| 2-bromo-6-nitroaniline | 2-bromo-6-nitrophenylguanidine |
| 2-iodo-6-nitroaniline | 2-iodo-6-nitrophenylguanidine |
| 2-fluoro-6-nitroaniline | 2-fluoro-6-nitrophenylguanidine |
| 2-nitro-6-trifluoromethylaniline | 2-nitro-6-trifluoromethylphenylguanidine |
| 2-nitro-6-methoxyaniline | 2-nitro-6-methoxyphenylguanidine |
| 2-cyano-6-chloroaniline | 2-cyano-6-chlorophenylguanidine |
| 2-methyl-6-chloroaniline | 2-methyl-6-chlorophenylguanidine |
| 2-methyl-6-bromoaniline | 2-methyl-6-bromophenylguanidine |
| 2-methyl-6-fluoroaniline | 2-methyl-6-fluorophenylguanidine |
| 2-methyl-6-nitroaniline | 2-methyl-6-nitrophenylguanidine |
| 2-methyl-6-trifluoromethylaniline | 2-methyl-6-trifluoromethylphenylguanidine |
| 2-methyl-6-cyanoaniline | 2-methyl-6-cyanophenylguanidine |
| 2-methyl-6-methylsulfonylaniline | 2-methyl-6-methylsulfonylphenylguanidine |
| 2,4-dimethylaniline | 2,4-dimethylphenylguanidine |
| 2,6-dimethylaniline | 2,6-dimethylphenylguanidine |
| 2-trifluoromethyl-6-chloroaniline | 2-trifluoromethyl-6-chlorophenylguanidine |
| 2-trifluoromethyl-6-bromoaniline | 2-trifluoromethyl-6-bromophenylguanidine |
| 2-trifluoromethyl-6-fluoroaniline | 2-trifluoromethyl-6-fluorophenylguanidine |
| 2-trifluoromethyl-6-nitroaniline | 2-trifluoromethyl-6-nitrophenylguanidine |
| 2-trifluoromethyl-4-chloroaniline | 2-trifluoromethyl-4-chlorophenylguanidine |
| 2-trifluoromethyl-4-bromoaniline | 2-trifluoromethyl-4-bromophenylguanidine |
| 2-trifluoromethyl-4-fluoroaniline | 2-trifluoromethyl-4-fluorophenylguanidine |
| 4-trifluoromethyl-2-chloroaniline | 4-trifluoromethyl-2-chlorophenylguanidine |
| 4-trifluoromethyl-2-bromoaniline | 4-trifluoromethyl-2-bromophenylguanidine |
| 4-trifluoromethyl-2-fluoroaniline | 4-trifluoromethyl-2-bromophenylguanidine |

-continued

| TABLE I | TABLE II |
|---|---|
| 2,4-dichloro-6-methylaniline | 2,4-dichloro-6-methylphenylguanidine |
| 2,6-dichloro-4-methylaniline | 2,6-dichloro-4-methylphenylguanidine |
| 3,5-ditrifluoromethylaniline | 3,5-ditrifluoromethylphenylguanidine |
| 2-methoxy-4-nitroaniline | 2-methoxy-4-nitrophenylguanidine |
| 2-trifluoromethyl-4-nitroaniline | 2-trifluoromethyl-4-nitrophenylguanidine |
| 2,4-dichloro-6-methoxyaniline | 2,4-dichloro-6-methoxyphenylguanidine |
| 2,6-dimethyl-4-chloroaniline | 2,6-dimethyl-4-chlorophenylguanidine |
| 2,6-dimethyl-4-fluoroaniline | 2,6-dimethyl-4-fluorophenylguanidine |
| 2,6-dimethyl-4-bromoaniline | 2,6-dimethyl-4-bromopenylguanidine |
| 2,6-dimethyl-4-nitroaniline | 2,6-dimethyl-4-nitrophenylguanidine |
| 2,6-dimethyl-4-trifluoromethylaniline | 2,6-dimethyl-4-trifluoromethylpenylguanidine |
| 2-ethyl-4-nitroaniline | 2-ethyl-4-nitrophenylguanidine |
| 2-ethyl-4-chloroaniline | 2-ethyl-4-chlorophenylguanidine |
| 2-ethyl-4-bromoaniline | 2-ethyl-4-bromophenylguanidine |
| 2-ethyl-4-fluoroaniline | 2-ethyl-4-fluorophenylguanidine |
| 2-ethyl-4-trifluoromethylaniline | 2-ethyl-4-trifluoromethylphenylguanidine |
| 2-ethyl-4-cyanoaniline | 2-ethyl-4-cyanophenylguanidine |
| 2-ethyl-4-methylsulfonylaniline | 2-ethyl-4-methylsulfonylphenylguanidine |
| 2,4-dichloro-6-bromoaniline | 2,4-dichloro-6-bromophenylguanidine |
| 2,6-dichloro-4-bromoaniline | 2,6-dichloro-4-bromophenylguanidine |
| 2,4-dibromo-6-chloroaniline | 2,4-dibromo-6-chlorophenylguanidine |
| 2,6-dibromo-4-chloroaniline | 2,6-dibromo-4-chlorophenylguanidine |
| 2,4-dichloro-6-fluoroaniline | 2,4-dichloro-6-fluorophenylguanidine |
| 2,6-dichloro-4-fluoroaniline | 2,6-dichloro-4-fluorophenylguanidine |
| 2,5-dichloro-4-fluoroaniline | 2,5-dichloro-4-fluorophenylguanidine |
| 2,4-dichloro-6-iodoaniline | 2,4-dichloro-6-iodophenylguanidine |
| 2,6-dichloro-4-iodoaniline | 2,6-dichloro-4-idophenylguanidine |
| 2,4-dibromo-6-iodoaniline | 2,4-dibromo-6-iodophenylguanidine |
| 2,4-dibromo-6-fluoroaniline | 2,4-dibromo-6-fluorophenylguanidine |
| 2,6-dibromo-4-fluoroaniline | 2,6-dibromo-4-fluorophenylguanidine |
| 2-chloro-4-bromo-6-fluoroaniline | 2-chloro-4-bromo-6-fluorophenylguanidine |
| 2-bromo-4-fluoro-6-chloroaniline | 2-bromo-4-fluoro-6-chlorophenylguanidine |
| 2-bromo-4-chloro-6-fluoroaniline | 2-bromo-4-chloro-6-fluorophenylguanidine |
| 2-chloro-4-iodo-6-bromoaniline | 2-chloro-4-iodo-6-bromophenylguanidine |
| 2,4,6-tribromoaniline | 2,4,6-tribromophenylguanidine |
| 2,4,6-trifluoroaniline | 2,4,6-trifluorophenylguanidine |

EXAMPLE 2

1-(2,6-Dichlorophenylamidino)-3-(t-butyl)urea

To a mixture of 10 g. (0.05 mole) of 2,6-dichlorophenylguanide and 10 ml xylene is added 5 g. of 5-butylisocyanate (0.05 mole) and the mixture is refluxed for 2 hours. The reaction product is cooled, triturated with heptane and filtered. Recrystallization from 1:1 isopropyl/water results in 1-(2,6-dichlorophenylamidino)-3-(t-butyl)urea.

When the above procedure is followed using the guanidines of Table II, Example 1, then the products prepared are shown in Table I below.

Table I 1-(o-chlorophenylamidino)-3-(t-butyl)urea
1-(m-chlorophenylamidino)-3-(t-butyl)urea
1-(p-chlorophenylamidino)-3-(t-butyl)urea
1-(2,3-dichlorophenylamidino)-3-(t-butyl)urea
1-(2,4-dichlorophenylamidino)-3-(t-butyl)urea
1-(2,5-dichlorophenylamidino)-3-(t-butyl)urea
1-(3,4-dichlorophenylamidino)-3-(t-butyl)urea
1-(3,5-dichlorophenylamidino)-3-t-butyl)urea
1-(2,3,4-trichlorophenylamidino)-3-(t-butyl)urea
1-(2,3,5-trichlorophenylamidino)-3-(t-butyl)urea
1-(2,3,6-trichlorophenylamidino)-3-(t-butyl)urea
1-(2,4,5-trichlorophenylamidino)-3-(t-butyl)urea
1-(2,4,6-trichlorophenylamidino)-3-(t-butyl)urea
1-(3,4,5-trichlorophenylamidino)-3-(t-butyl)urea
1-(o-bromophenylamidino)-3-(t-butyl)urea
1-(m-bromophenylamidino)-3-(t-butyl)urea
1-(p-bromophenylamidino)-3-(t-butyl)urea
1-(2,3-dibromophenylamidino)-3-(t-butyl)urea
1-(2,4-dibromophenylamidino)-3-(t-butyl)urea
1-(2,5-dibromophenylamidino)-3-(t-butyl)urea
1-(2,6-dibromophenylamidino)-3-(t-butyl)urea
1-(3,4-dibromophenylamidino)-3-(t-butyl)urea
1-(3,5-dibromophenylamidino)-3-(t-butyl)urea
1-(2-chloro-3-bromophenylamidino)-3-(t-butyl)urea
1-(2-chloro-4-bromophenylamidino)-3-(t-butyl)urea
1-(2-chloro-5-bromophenylamidino)-3-(t-butyl)urea
1-(2-chloro-6-bromophenylamidino)-3-(t-butyl)urea
1-(3-chloro-2-bromophenylamidino)-3-(t-butyl)urea
1-(3-chloro-4-bromophenylamidino)-3-(t-butyl)urea
1-(3-chloro-5-bromophenylamidino)-3-(t-butyl)urea
1-(3-chloro-6-bromophenylamidino)-3-(t-butyl)urea
1-(4-chloro-2-bromophenylamidino)-3-(t-butyl)urea
1-(4-chloro-3-bromophenylamidino)-3-(t-butyl)urea
1-(2-fluoro-4-chlorophenylamidino)-3-(t-butyl)urea
1-(2-fluoro-6-chlorophenylamidino)-3-(t-butyl)urea
1-(2-chloro-4-fluorophenylamidino)-3-(t-butyl)urea
1-(2-fluoro-6-bromophenylamidino)3-(t-butyl)urea
1-(2-bromo-4-fluorophenylamidino)-3-(t-butyl)urea
1-(2-iodo-4-chlorophenylamidino)-3-(t-butyl)urea
1-(2-iodo-6-chlorophenylamidino)-3-(t-butyl)urea
1-(2-chloro-4-iodophenylamidino)-3-(t-butyl)urea
1-(2-iodo-4-bromophenylamidino)-3-(t-butyl)urea
1-(o-fluorophenylamidino)-3-(t-butyl)urea
1-(m-fluorophenylamidino)-3-(t-butyl)urea
1-(p-fluorophenylamidino)-3-(t-butyl)urea
1-(p-iodophenylamidino)-3-(t-butyl)urea
1-(2,4-difluorophenylamidino)-3-(t-butyl)urea
1-(2,5-difluorophenylamidino)-3-(t-butyl)urea
1-(2,6-difluorophenylamidino)-3-(t-butyl)urea
1-(2,4-diiodophenylamidino)-3-(t-butyl)urea
1-(2-iodo-6-bromophenylamidino)-3-(t-butyl)urea
1-(2-bromo-4-iodophenylamidino)-3-(t-butyl)urea
1-(2-fluoro-4-iodophenylamidino)-3-(t-butyl)urea
1-(2-iodo-4-fluorophenylamidino)-3-(t-butyl)urea
1-(2trifluoromethylphenylamidino)-3-(t-butyl)urea
1-(m-trifluoromethylphenylamidino)-3-(t-butyl)urea
1-(p-trifluoromethylphenylamidino)-3-(t-butyl)urea
1-(p-trifluoromethoxyphenylamidino)-3-(t-butyl)urea
1-(p-methylsulfonylphenylamidino)-3-(t-butyl)urea
1-(o-nitrophenylamidino)-3-(t-butyl)urea
1-(m-nitrophenylamidino)-3-(t-butyl)urea 1-(p-nitrophenylamidino)-3-(t-butyl)urea
1-(2-chloro-4-nitrophenylamidino)-3-(t-butyl)urea
1-(2-bromo-4-nitrophenylamidino)-3-(t-butyl)urea
1-(2-iodo-4-nitrophenylamidino)-3-(t-butyl)urea
1-(2-fluoro-4-nitrophenylamidino)-3-(t-butyl)urea
1-(2nitro-4-chlorophenylamidino)-3-(t-butyl)urea
1-(2-nitro-4-bromophenylamidino)-3-(t-butyl)urea
1-(2-nitro-4-fluorophenylamidino)-3-(t-butyl)urea
1-(2-nitro-4-trifluoromethylphenylamidino)-3-(t-butyl)urea
1-(2-nitro-4-methoxyphenylamidino)-3-(t-butyl)urea
1-(2-cyano-4-chlorophenylamidino)-3-(t-butyl)urea
1-(2chloro-4-cyanophenylamidino)-3-(t-butyl)urea
1-(2-methyl-4-chlorophenylamidino)-3-(t-butyl)urea
1-(2-methyl-4-bromophenylamidino)-3-(t-butyl)urea
1-(2-methyl-4-fluorophenylamidino)-3-(t-butyl)urea
1-(2-chloro-4-methylphenylamidino)-3-(t-butyl)urea
1-(2-bromo-4-methylphenylamidino)-3-(t-butyl)urea
1-(2-fluoro-4-methylphenylamidino)-3-(t-butyl)urea
1-(2-cyano-4-methylphenylamidino)-3-(t-butyl)urea
1-(2-trifluoromethyl-4-methylphenylamidino)-3-(t-butyl)urea
1-(2-methyl-4-nitrophenylamidino)-3-(t-butyl)urea
1-(2-methyl-4-cyanophenylamidino)-3-(t-butyl)urea
1-(2-methyl-4-trifluoromethylphenylamidino)-3-(t-butyl)urea
1-(2-chloro-6-nitrophenylamidino)-3-(t-butyl)urea
1-(2-bromo-6-nitrophenylamidino)-3-(t-butyl)urea
1-(2-iodo-6-nitrophenylamidino)-3-(t-butyl)urea
1-(2-fluoro-6-nitrophenylamidino)-3-(t-butyl)urea
1-(2-nitro-6-trifluoromethylphenylamidino)-3-(t-butyl)urea
1-(2-nitro-6-methoxyphenylamidino)-3-(t-butyl)urea
1-(2-cyano-6-chlorophenylamidino)-3-(t-butyl)urea
1-(2-methyl-6-chlorophenylamidino)-3-(t-butyl)urea
1-(2-methyl-6-bromophenylamidino)-3-(t-butyl)urea
1-(2-methyl-6-fluorophenylamidino)-3-(t-butyl)urea
1-(2-methyl-6-nitrophenylamidino)-3-(t-butyl)urea
1-(2-methyl-6-trifluoromethylphenylamidino)-3-(t-butyl)urea
1-(2-methyl-6-cyanophenylamidino)-3-(t-butyl)urea
1-(2-methyl-6-methylsulfonylphenylamidino)-3-(t-butyl)urea
1(2,4-dimethylphenylamidino)-3-(t-butyl)urea
1-(2,6-dimethylphenylamidino)-3-(t-butyl)urea
1-(2-trifluoromethyl-6-chlorophenylamidino)-3-(t-butyl)urea
1-(2-trifluoromethyl-6-bromophenylamidino)-3-(t-butyl)urea
1-(2-trifluoromethyl-6-fluorophenylamidino)-3-(t-butyl)urea
1-(2-trifluoromethyl-6-nitrophenylamidino)-3-(t-butyl)urea
1-(2-trifluoromethyl-4-chlorophenylamidino)-3-(t-butyl)urea
1-(2-trifluoromethyl-4-bromophenylamidino)-3-(t-butyl)urea
1-(2-trifluoromethyl-4-fluorophenylamidino)-3-(t-butyl)urea
1-(4-trifluoromethyl-2-chlorophenylamidino)-3-(t-butyl)urea
1-(4-trifluoromethyl-2-bromophenylamidino)-3-(t-butyl)urea
1-(4-trifluoromethyl-2-bromophenylamidino)-3-(t-butyl)urea
1-(2,4-dichloro-6-methylphenylamidino)-3-(t-butyl)urea
1-(2,6-dichloro-4-methylphenylamidino)-3-(t-butyl)urea
1-(3,5-ditrifluoromethylphenylamidino)-3-(t-butyl)urea
1-(2-methoxy-4-nitrophenylamidino)-3-(t-butyl)urea
1-(2-trifluoromethyl-4-nitrophenylamidino)-3-(t-butyl)urea
1-(2,4-dichloro-6-methoxyphenylamidino)-3-(t-butyl)urea
1-(2,6-dimethyl-4-chlorophenylamidino)-3-(t-butyl)urea
1-(2,6-dimethyl-4-fluorophenylamidino)-3-(t-butyl)urea
1-(2,6-dimethyl-4-bromophenylamidino)-3-(t-butyl)urea
1-(2,6-dimethyl-4-nitrohenylamidino-3-(t-butyl)urea
1-(2,6-dimethyl-4-trifluoromethylphenylamidino)-3-(t-butyl)urea
1-(2-ethyl-4-nitrophenylamidino-3-(t-butyl)urea
1-(2-ethyl-4-chlorophenylamidino)-3-(t-butyl)urea
1-(2-ethyl-4-bromophenylamidino)-3-(t-butyl)urea
1-(2-ethyl-4-fluorophenylamidino)-3-(t-butyl)urea
1-(2-ethyl-4-trifluoromethylphenylamidino)-3-(t-butyl)urea
1-(2-ethyl-4-cyanophenylamidino)-3-(t-butyl)urea
1-(2-ethyl-4-methylsulfonylphenylamidino)-3-(t-butyl)urea
1-(2,4-dichloro-6-bromophenylamidino)-3-(t-butyl)urea
1-(2,6-dichloro-4-bromophenylamidino)-3-(t-butyl)urea
1-(2,4-dibromo-6-chlorophenylamidino)-3-(t-butyl)urea
1-(2,6-dibromo-4-chlorophenylamidino)-3-(t-butyl)urea
1-(2,4-dichloro-6-fluorophenylamidino)-3-(t-butyl)urea
1-(2,6-dichloro-4-fluorophenylamidino)-3-(t-butyl)urea
1-(2,5-dichloro-4-fluorophenylamidino)-3-(t-butyl)urea
1-(2,4-dichloro-6-iodophenylamidino)-3-(t-butyl)urea
1-(2,6-dichloro-4-iodophenylamidino)-3-(t-butyl)urea
1-(2,4-dibromo-6-iodophenylamidino)-3-(t-butyl)urea
1-(2,4-dibromo-6-fluorophenylamidino)-3-(t-butyl)urea
1-(2,6-dibromo-4-fluorophenylamidino)-3-(t-butyl)urea
1-(2-chloro-4-bromo-6-fluorophenylamidino)-3-(t-butyl)urea
1-(2-bromo-4-fluoro-6-chlorophenylamidino)-3-(t-butyl)urea
1-(2-bromo-4-chloro-6-fluorophenylamidino)-3-(t-butyl)urea
1-(2-chloro-4-iodo-6-bromophenylamidino)-3-(t-butyl)urea
1-(2,4,6-tribromophenylamidino)-3-(t-butyl)urea
1-(2,4,6-trifluorophenylamidino)-3-(t-butyl)urea

EXAMPLE 3

(2,6-Dichlorophenylamidino)urea hydrochloride

A mixture of 32.1 g. (0.106 moles) of 1-(2,6-dichlorophenylamidino)-3-(t-butyl)urea and 200 ml of conc. hydrochloric acid is refluxed for ½ hour. The reaction mixture is cooled, filtered and washed with 10 ml of 1:1 HCl/H$_2$O and dried. The product is then recrystallized from ethanol-ether to obtain (2,6-dichlorophenylamidino)urea hydrochloride.

In a similar manner other desired salts may be prepared using the appropriate acid.

The free base is prepared according to Example 1.

When the above procedure is followed using the amidinoureas of Table I, Example 2, then the corresponding amidinourea of Table I is prepared as follows.

TABLE I (o-chlorophenylamidino)urea
(m-chlorophenylamidino)urea
(p-chlorophenylamidino)urea
(2,3-dichlorophenylamidino)urea
(2,4-dichlorophenylamidino)urea
(2,5-dichlorophenylamidino)urea (3,4-dichlorophenylamidino)urea
(3,5-dichlorophenylamidino)urea
(2,3,4-trichlorophenylamidino)urea
(2,3,5-trichlorophenylamidino)urea
(2,3,6-trichlorophenylamidino)urea
(2,4,5-trichlorophenylamidino)urea
(2,4,6-trichlorophenylamidino)urea
(3,4,5-trichlorophenylamidino)urea
(o-bromophenylamidino)urea
(m-bromophenylamidino)urea
p-bromophenylamidino)urea
(2,3-dibromophenylamidino)urea
(2,4-dibromophenylamidino)urea
(2,5-dibromophenylamidino)urea
(2,6-dibromophenylamidino)urea
(3,4-dibromophenylamidino)urea
(3,5-dibromophenylamidino)urea
(2-chloro-3-bromophenylamidino)urea
(2-chloro-4-bromophenylamidino)urea
(2-chloro-5-bromophenylamidino)urea
(2-chloro-6-bromophenylamidino)urea
(3-chloro-2-bromophenylamidino)urea
(3-chloro-4-bromophenylamidino)urea
(3-chloro-5-bromophenylamidino)urea
(3-chloro-6-bromophenylamidino)urea
(4-chloro-2-bromophenylamidino)urea
(4-chloro-3-bromophenylamidino)urea
(2-fluoro-4-chlorophenylamidino)urea
(2-fluoro-6-chlorophenylamidino)urea
(2-chloro-4-fluorophenylamidino)urea
(2-fluoro-6-bromophenylamidino)urea
(2-bromo-4-fluorophenylamidino)urea
(2-iodo-4-chlorophenylamidino)urea
(2-iodo-6-chlorophenylamidino)urea
(2-chloro-4-iodophenylamidino)urea
(2-iodo-4-bromophenylamidino)urea
(o-fluorophenylamidino)urea
(m-fluorophenylamidino)urea
(p-fluorophenylamidino)urea
(p-iodophenylamidino)urea
(2,4-difluorophenylamidino)urea
(2,5-difluorophenylamidino)urea
(2,6-difluorophenylamidino)urea
(2,4-diiodophenylamidino)urea
(2-iodo-6-bromophenylamidino)urea
(2-bromo-4-iodophenylamidino)urea
(2-fluoro-4-iodophenylamidino)urea
(2-iodo-4-fluorophenylamidino)urea
(2-trifluoromethylphenylamidino)urea
(m-trifluoromethylphenylamidino)urea
(p-trifluoromethylphenylamidino)urea
(p-trifluoromethoxyphenylamidino)urea
(p-methylsulfonylphenylamidino)urea
(o-nitrophenylamidino)urea
(m-nitrophenylamidino)urea
(p-nitrophenylamidino)urea
(2-chloro-4-nitrophenylamidino)urea
(2-bromo-4-nitrophenylamidino)urea
(2-iodo-4-nitrophenylamidino)urea
(2-fluoro-4-nitrophenylamidino)urea
(2-nitro-4-chlorophenylamidino)urea
(2-nitro-4-bromophenylamidino)urea
(2-nitro-4-fluorophenylamidino)urea
(2-nitro-4-trifluoromethylphenylamidino)urea
(2-nitro-4-methoxyphenylamidino)urea
(2-cyano-4-chlorophenylamidino)urea
(2-chloro-4-cyanophenylamidino)urea
(2-methyl-4-chlorophenylamidino)urea
(2-methyl-4-bromophenylamidino)urea
(2-methyl-4-fluorophenylamidino)urea
(2-chloro-4-methylphenylamidino)urea
(2-bromo-4-methylphenylamidino)urea
(2-fluoro-4-methylphenylamidino)urea
(2-cyano-4-methylphenylamidino)urea
(2-trifluoromethyl-4-methylphenylamidino)urea
(2-methyl-4-nitrophenylamidino)urea
(2-methyl-4-cyanophenylamidino)urea
(2-methyl-4-trifluoromethylphenylamidino)urea
(2-chloro-6-nitrophenylamidino)urea
(2-bromo-6-nitrophenylamidino)urea
(2-iodo-6-nitrophenylamidino)urea
(2-fluoro-6-nitrophenylamidino)urea
(2-nitro-6-trifluoromethylphenylamidino)urea
(2-nitro-6-methoxyphenylamidino)urea
(2-cyano-6-chlorophenylamidino)urea
(2-methyl-6-chlorophenylamidino)urea
(2-methyl-6-bromophenylamidino)urea
(2-methyl-6-fluorophenylamidino)urea
(2-methyl-6-nitrophenylamidino)urea
(2-methyl-6-trifluoromethylphenylamidino)urea
(2-methyl-6-cyanophenylamidino)urea
(2-methyl-6-methylsulfonylphenylamidino)urea
(2,4-dimethylphenylamidino)urea
(2,6-dimethylphenylamidino)urea
(2-trifluoromethyl-6-chlorophenylamidino)urea
(2-trifluoromethyl-6-bromophenylamidino)urea
(2-trifluoromethyl-6-fluorophenylamidino)urea
(2-trifluoromethyl-6-nitrophenylamidino)urea
(2-trifluoromethyl-4-chlorophenylamidino)urea
(2-trifluoromethyl-4-bromophenylamidino)urea
(2-trifluoromethyl-4-fluorophenylamidino)urea
(4-trifluoromethyl-2-chlorophenylamidino)urea
(4-trifluoromethyl-2-bromophenylamidino)urea
(4-trifluoromethyl-2-fluorophenylamidino)urea
(4-trifluoromethyl-2-bromophenylamidino)urea
(2,4-dichloro-6-methylphenylamidino)urea
(2,6-dichloro-4-methylphenylamidino)urea
(3,5-ditrifluoromethylphenylamidino)urea
(2-methoxy-4-nitrophenylamidino)urea
(2-trifluoromethyl-4-nitrophenylamidino)urea
(2,4-dichloro-6-methoxyphenylamidino)urea
(2,6-dimethyl-4-chlorophenylamidino)urea
(2,6-dimethyl-4-fluorophenylamidino)urea
(2,6-dimethyl-4-bromophenylamidino)urea
(2,6-dimethyl-4-nitrophenylamidino)urea
(2,6-dimethyl-4-trifluoromethylphenylamidino)urea
(2-ethyl-4-nitrophenylamidino)urea
(2-ethyl-4-chlorophenylamidino)urea
(2-ethyl-4-bromophenylamidino)urea
(2-ethyl-4-fluorophenylamidino)urea
(2-ethyl-4-trifluoromethylphenylamidino)urea
(2-ethyl-4-cyanophenylamidino)urea
(2-ethyl-4-methylsulfonylphenylamidino)urea
(2,4-dichloro-6-bromophenylamidino)urea
(2,6-dichloro-4-bromophenylamidino)urea
(2,4-dibromo-6-chlorophenylamidino)urea
(2,6-dibromo-4-chlorophenylamidino)urea
(2,4-dichloro-6-fluorophenylamidino)urea
(2,6-dichloro-4-fluorophenylamidino)urea
(2,5-dichloro-4-fluorophenylamidino)urea
(2,4-dichloro-6-iodophenylamidino)urea
(2,6-dichloro-4-iodophenylamidino)urea
(2,4-dibromo-6-iodophenylamidino)urea
(2,4-dibromo-6-fluorophenylamidino)urea
(2,6-dibromo-4-fluorophenylamidino)urea
(2-chloro-4-bromo-6-fluorophenylamidino)urea
(2-bromo-4-fluoro-6-chlorophenylamidino)urea (2-bromo-4-chloro-6-fluorophenylamidino)urea
(2-chloro-4-iodo-6-bromophenylamidino)urea
(2,4,6-tribromophenylamidino)urea
(2,4,6-trifluorophenylamidino)urea

I claim:

1. A method for the treatment of cardiovascular disorders which comprises administering to a patient a therapeutically effective amount of at least one of the compounds of the formula:

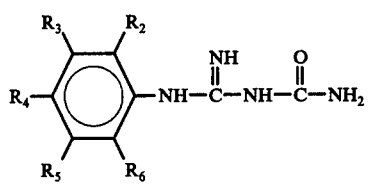

where:

$R_2$, $R_3$, $R_4$, $R_5$ and $R_6$ may be the same or different and are hydrogen provided at least one of $R_2$, $R_3$, $R_4$, $R_5$ and $R_6$ is other than hydrogen. halo, haloloweralkyl, nitro, cyano, loweralkylsulfonyl, loweralkoxy or loweralkyl; and the non-toxic acid addition salts thereof.

2. A method according to claim 1 wherein the compound is of the formula:

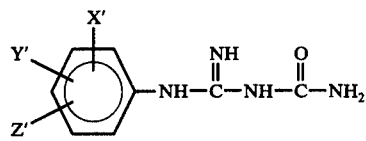

where:

X', Y' and Z' may be the same or different and are hydrogen provided at least one of X', Y' and Z' is other than hydrogen, halo, haloloweralkyl, nitro, cyano, loweralkylsulfonyl, loweralkoxy or loweralkyl.

3. A method according to claim 2 where:

X', Y' and Z' are hydrogen provided at least one of X', Y' and Z' is other than hydrogen, halo, haloloweralkyl or loweralkyl.

4. A method according to claim 3 where:

X' is hydrogen, chloro, bromo or fluoro;
Y' is hydrogen, chloro, methyl or trifluoromethyl;
Z' is chloro, bromo, fluoro, methyl or trifluoromethyl.

5. A method according to claim 4 where the compound is selected from the group consisting of o-chlorophenylamidinourea
m-chlorophenylamidinourea
p-chlorophenylamidinourea
(2,3-dichlorophenylamidino)urea
(2,4-dichlorophenylamidino)urea
(2,5-dichlorophenylamidino)urea
(2,6-dichlorophenylamidino)urea
(3,4-dichlorophenylamidino)urea
(3,5-dichlorophenylamidino)urea.

6. A method according to claim 5 where the compound is (2,6-dichlorophenylamidino)urea.

* * * * *